United States Patent
Kikuyama et al.

(10) Patent No.: US 7,268,256 B2
(45) Date of Patent: Sep. 11, 2007

(54) METHOD OF PURIFYING QUATERNARY ALKYL AMMONIUM SALT AND QUATERNARY ALKYL AMMONIUM SALT

(75) Inventors: Hirohisa Kikuyama, Osaka (JP); Masahide Waki, Osaka (JP); Shinji Hashiguchi, Osaka (JP); Tetsuo Nishida, Osaka (JP); Yasutaka Tashiro, Osaka (JP); Kenji Aoki, Osaka (JP)

(73) Assignee: Stella Chemifa Kabushiki Kaisha, Osaka (JP)

( * ) Notice: Subject to any disclaimer, the term of this patent is extended or adjusted under 35 U.S.C. 154(b) by 130 days.

(21) Appl. No.: 10/514,192

(22) PCT Filed: Apr. 17, 2003

(86) PCT No.: PCT/JP03/04911

§ 371 (c)(1),
(2), (4) Date: Jun. 13, 2005

(87) PCT Pub. No.: WO03/095414

PCT Pub. Date: Nov. 20, 2003

(65) Prior Publication Data

US 2006/0020147 A1    Jan. 26, 2006

(30) Foreign Application Priority Data

May 14, 2002  (JP) .............................. 2002-138918

(51) Int. Cl.
C07C 211/62      (2006.01)
C07C 209/84      (2006.01)
(52) U.S. Cl. ..................................... 564/296
(58) Field of Classification Search ................ 564/296
See application file for complete search history.

(56) References Cited

U.S. PATENT DOCUMENTS

| | | | | |
|---|---|---|---|---|
| 3,227,755 A | * | 1/1966 | Bragdon et al. | 564/8 |
| 3,472,740 A | * | 10/1969 | Boothe | 203/37 |
| 3,928,447 A | * | 12/1975 | Chen et al. | 564/296 |
| 4,216,168 A | * | 8/1980 | Evans et al. | 564/8 |
| 5,929,280 A | * | 7/1999 | Nonaka et al. | 564/296 |

FOREIGN PATENT DOCUMENTS

| | | |
|---|---|---|
| JP | 2002-30044 | 1/2002 |
| JP | 2002-53532 | 2/2002 |
| JP | 2003-137847 | 5/2003 |

OTHER PUBLICATIONS

The Merck Index 12th ed. (1996), Susan Budavari (ed.), Merck & Co., Inc., Whitehouse Station, NJ, p. 1576, entry No. 9364.*
Database CAPLUS on STN, Acc. No. 1975:413320, Kato et al., JP 49105927 (Oct. 7, 1974) (abstract).*

* cited by examiner

*Primary Examiner*—Brian Davis
(74) *Attorney, Agent, or Firm*—Young & Thompson

(57) ABSTRACT

Provided is a method for purifying a quaternary alkyl ammonium salt enabling the obtainment of a particulate quaternary alkyl ammonium salt having a low water content at a high yield which is suitably used as an electrolyte in an electrolytic solution.

The method for the purification of a quaternary alkyl ammonium salt comprises dispersing a quaternary alkyl ammonium salt to be purified into an organic solvent to allow it to form a suspension there. The alkyl groups constituting the quaternary alkyl ammonium salt have 1 to 5 carbon atoms each. The quaternary alkyl ammonium salt to be purified is dispersed into the organic solvent to make a suspension, and then the particles are washed with an alcohol solvent.

9 Claims, No Drawings

METHOD OF PURIFYING QUATERNARY ALKYL AMMONIUM SALT AND QUATERNARY ALKYL AMMONIUM SALT

This application is a National Stage of PCT/JP03/04911, filed Apr. 17, 2003, and claims priority to JP 2002-138918, filed May 14, 2002.

TECHNICAL FIELD

The present invention relates to a method for purifying a quaternary alkyl ammonium salt, and to a purified quaternary alkyl ammonium salt, more specifically to a method for purifying a quaternary alkyl ammonium salt which is suitably used as an electrolyte in an organic electrolytic solution incorporated in a dielectric capacitor or battery, particularly to a method for purifying triethylmethylammonium tetrafluoroborate.

BACKGROUND ART

Conventionally, in order to produce a quaternary alkyl ammonium salt, for example, to produce quaternary alkyl ammonium tetrafluoroborate, quaternary alkyl ammonium chloride, bromide or hydroxide is allowed to react with fluoroboric acid. Such methods have been proposed in U.S. Pat. No. 3,965,178 (1976), and published Japanese Patent Applications, Publication No. S63(1988)-30454, 2000-226361, and 2001-247522.

A published Japanese Patent Application, Publication No. H5(1993)-286981 proposes a method involving the use of anhydrous hydrofluoric acid. An published Japanese Patent Application, Publication No. H11(1999)-310555 proposes yet another method in which a hydrogenfluoride salt of quaternary alkyl ammonium fluoride and boron trifluoride or its complex are allowed to react. A published Japanese Patent Application, Publication No. H11(1999)-27179 proposes yet another method in which tertiary amine is allowed to react with alkyl halide, which is immediately followed by reaction with fluoroboric acid. A published Japanese Patent Application, Publication No. H11(1999)-315055 proposes yet another method in which quaternary alkyl ammonium bicarbonate and fluoroboric acid are allowed to react.

A quaternay alkyl ammonium salt (e.g., quaternary alkyl ammonium tetrafluoroborate) obtained by one of the conventional methods described above contains a trace amount of chlorine or bromine derived from a starting material, or of fluoroboric acid which is introduced during the synthetic process. If such a salt is not properly treated so as to be deprived of those contaminants, the salt could hardly be used with profit as an electrolyte in an organic electrolytic solution of a dielectric capacitor or battery. The method for treating such a salt to improve its purity includes purification based on recrystallization which, however, can hardly achieve the complete elimination of contaminants.

A published Japanese Patent Application, Publication No. 2001-348388 discloses a method in which quaternary alkyl ammonium halide is allowed to react with fluoroboric acid in alcohol, and the reaction product is dried. This method enables the elimination of chlorine or bromine contaminant derived from the starting material, and thus the obtainment of a quaternary alkyl ammonium salt in which contaminants derived from the starting materials are significantly inhibited.

A quaternary alkyl ammonium salt obtained by this method, however, tends to conglomerate as do quaternary alkyl ammonium salts obtained by the conventional methods described above. Because of this tendency, the salt in question poses following problems.

Quaternary alkyl ammonium salts are generally highly hygroscopic. Because of this property, quaternary alkyl ammonium salts obtained by the conventional methods tend to conglomerate, which reduces the drying efficiency of the salts. If such a quaternary alkyl ammonium salt is used as an electrolyte in an electrolytic solution of an electric circuit element, it will react with water to produce an acid in the electrolytic solution which will result in the augmented internal resistance if the circuit element is a battery, or corrode the metal parts, if the circuit element is a dielectric capacitor.

An object of the present invention is to solve the problems inherent to the conventional methods. To put it more specifically, the object of the present invention is to provide a method for producing highly pure quaternary alkyl ammonium salts which can be profitably used in the production of dielectric capacitors.

DISCLOSURE OF THE INVENTION

The present inventors studied hard to achieve the above object, and found that it is possible to give a solution to the problems by providing a particulate moisture-deprived quaternary alkyl ammonium salt which is brought about by preparing a quaternary alkyl ammonium salt, and dispersing it in an organic solvent to make it a suspension. This finding led to the present invention.

The present invention provides a method for purifying a quaternary alkyl ammonium salt, the method comprising the step of dispersing a quaternary alkyl ammonium salt to be purified in an organic solvent to make it a suspension.

The present invention also provides particulate quaternary alkyl ammonium salts.

(Operation)

When a quaternary alkyl ammonium salt to be purified is transferred to an organic solvent, it will disperse into the organic solvent to become a suspension, even if it exists as a solid mass before the transference. The suspension is filtered to provide a highly pure quaternary alkyl ammonium in the form of particles.

BEST MODE FOR CARRYING OUT THE INVENTION

The present invention will be described in detail below.

(Quaternary Alkyl Ammonium Salt)

The alkyl groups constituting a quaternary alkyl ammonium salt to be purified by the inventive method are not limited to any specific ones. However, from the viewpoint of obtaining a quaternary alkyl ammonium salt with improved electrochemical properties, particularly of obtaining a salt with an enlarged oxidation-reduction potential, alkyl groups with 1 to 5 carbon atoms are preferred. Thus, suitable exemplary alkyl groups include methyl, ethyl, n-propyl, sec-propyl, n-butyl, sec-butyl, tert-butyl, n-pentyl, sec-pentyl, tert-pentyl, etc.

The alkyl groups may be the same with each other. However, from the viewpoint of ensuring an improved effect of the inventive method, or of obtaining a quaternary alkyl ammonium salt with an improved oxidation-reduction potential, at least two of the alkyl groups are preferably different from each other.

One or more of the alkyl groups may be substituted by other substituent(s), unless the substitution interferes with the effect of the invention. Suitable substituents include, for example, benzoic substituent(s) such as benzyl or phenyl, or pyridinium. Among them, pyridinium is particularly preferred.

Suitable exemplary quaternary alkyl ammonium salts to be purified by the inventive method include quaternary alkyl ammonium-tetrafluoroborates, quaternary alkyl ammonium-hexafluorophosphates, quaternary alkyl ammonium-hexafluoroantimonates, quaternary alkyl ammonium-hexafluoroarsenates, etc. However, from the viewpoint of desirable electrochemical properties such as (1) high electric conductivity, (2) high oxidation-reduction potential, and (3) wide range of tolerable temperatures, quaternary alkyl ammonium-tetrafluoroborates and quaternary alkyl ammonium-hexafluorophosphates are more preferable, and quaternary alkyl ammonium-tetrafluoroborates are most preferable.

Among quaternary alkyl ammonium-tetrafluoroborates, the followings are preferred because of their ensuring the effect of the inventive method. They are triethylmethylammonium tetrafluoroborate, ethyltrimethylammonium tetrafluoroborate, tripropylmethylammonium tetrafluoroborate, tributylmethylammonium tetrafluoroborate, N-ethyl-N-methylpyrrolidinium tetrafluoroborate, and N,N-dimethylenepyrrolidinium tetrafluoroborate. Among them, triethylmethylammonium tetrafluoroborate is particularly preferred.

(Quaternary Alkyl Ammonium Salt to be Purified)

The quaternary alkyl ammonium salt to be purified refers herein to a quaternary alkyl ammonium salt to be purified by the inventive method.

A quaternary alkyl ammonium salt to be purified is not limited to any specific one, but may include any quaternary alkyl ammonium salts obtained by any known methods. The following quaternary alkyl ammonium salts obtained by the methods described below may be purified by the inventive method.

Needless to say, any quaternary alkyl ammonium salts other than those described above which happen to contain impurities for unknown reasons may be purified by the inventive method. Even a previously purified quaternary alkyl ammonium salt may be purified by the inventive method to further enhance its purity.

The quaternary alkyl ammonium salts to be purified by the inventive method include those obtained by the following known methods.

(1) Synthesis method in which quaternary alkyl ammonium chloride, bromide or hydroxide is allowed to react with fluoroboric acid (U.S. Pat. No. 3,965,178, published Japanese Patent Applications, Publication No. S63(1988)-30454, 2000-226361 and 2001-247522).

(2) Synthesis method using hydrofluoric acid anhydride (a published Japanese Patent Application, Publication No. H5(1993)-286981)

(3) Synthesis method in which a hydrofluoric acid salt of quaternary alkyl ammonium fluoride is allowed to react with boron trifluoride or its complex (A published Japanese Patent Application, Publication No. H11(1999)-310555).

(4) Synthesis method in which tertiary amine is allowed to react with alkyl halide and the reaction product is immediately allowed to react with fluoroboric acid (A published Japanese Patent Application Publication No. H11(1999)-27179).

(5) Synthesis method in which quaternary alkyl ammonium bicarbonate is allowed to react with fluoroboric acid (A published Japanese Patent Application, Publication No. H11 (1999)-315055).

(6) Synthesis method disclosed in an examined Japanese Patent Application, Publication No. H7(1995)-116113.

(7) Synthesis method in which quaternary alkyl ammonium halide is allowed to react with fluoroboric acid in alcohol, and the reaction product is dried (A published Japanese Patent Application, Publication No. 2001-348388).

(Impurities in a Quaternary Alkyl Ammonium Salt to be Purified)

Impurities accompanying a quaternary alkyl ammonium salt to be purified are roughly divided into two categories according to their sources: (1) those from starting materials, and (2) those introduced during the purification process represented by moisture.

(Impurities from Starting Materials)

If an inadequately purified quaternary alkyl ammonium salt is used as an electrolyte in an electrolytic solution of a dielectric capacitor, the capacitor will have an augmented internal resistance which will case an energy loss as a result of voltage drop each time electricity is charged into or discharged from the capacitor. Then, it will become impossible to maximally exploit the electrochemical property of the quaternary alkyl ammonium salt. Moreover, such a quaternary alkyl ammonium salt will react with water to produce an acid in the electrolytic solution which will corrode the metal parts of the dielectric capacitor.

Impurities derived from starting materials and brought into as a result of synthesis may include, for example, followings.

The synthesis method disclosed in a published Japanese Patent Application, Publication No. H11(1999)-310555 uses quaternary ammonium fluoride as an intermediate. Thus, a quaternary alkyl ammonium salt produced by this method is abundantly contaminated with hydrofluoric acid. The most important contaminant here is hydrofluoric acid.

In the synthesis method disclosed in an examined Japanese Patent Application, Publication No. H7(1995)-116113, turn-over of tertiary amines remains often low. Thus, tertiary alkyl ammonium alkyl carbonate is contaminated with tertiary amine and dialkyl carbonate or compounds used as starting materials. In this method, the important contaminants are tertiary amine and dialkyl carbonate.

In addition, when a quaternary alkyl ammonium alkyl carbonate containing secondary amine is allowed to react with fluoroboric acid, tertiary amine tetrafluoroborate is produced as well as quaternary alkyl ammonium tetrafluoroborate. In this case, the most important contaminant is tertiary amine tetrafluoroborate.

[Moisture]

As mentioned above, according to the method disclosed in a published Japanese Patent Application, Publication No. 2001-348388, quaternary alkyl ammonium halide is allowed to react with fluoroboric acid in alcohol, and the reaction product is dried. This method enables the elimination of chlorine or bromine contaminant derived from the starting material, and thus the obtainment of a quaternary alkyl ammonium salt in which contaminants derived from starting materials are significantly inhibited.

When a quaternary alkyl ammonium salt obtained by reacting quaternary alkyl ammonium halide with fluoroboric acid is used as a starting material to be purified by the inventive method, it will be possible to obtain a quaternary alkyl ammonium salt having a far higher purity than is possible with the usage of quaternary alkyl ammonium salts obtained by other conventional methods. Similarly, when quaternary alkyl ammonium hydroxide is allowed to react with fluoroboric acid, it is possible to obtain a quaternary alkyl ammonium salt comparatively free from impurities. The effect is notable, and the principal reaction is preferably allowed to occur in alcohol.

This method is based on the reaction between quaternary alkyl ammonium halide and fluoroboric acid.

A quaternary alkyl ammonium salt produced by the method described in a published Japanese Patent Application Publication No. 2001-348388 is comparatively free from impurities derived from starting materials. However, a quaternary alkyl ammonium salt obtained by this method tends to conglomerate, which reduces the drying efficiency of the salt. Therefore, the water content of the salt increases. Then, it will become impossible to maximally exploit the electrochemical property of the salt. To avoid this, it is necessary to minimize the water content of the quaternary alkyl ammonium salt. If it is possible to obtain a quaternary alkyl ammonium salt in the form of particles instead of a solid mass, it will be possible to maximally exploit the electrochemical properties of the salt because the particulate salt will dry faster and have a more reduced water content than the solid counterpart.

The inventive method aims to obtain a quaternary alkyl ammonium salt as a particulate crystal, the method comprising obtaining a quaternary alkyl ammonium salt, and dispersing it into an organic solvent to make it a suspension. It is possible by this method to obtain a quaternary alkyl ammonium salt which ensures the improved efficiency of drying, and has a comparatively low water content.

Before being deformed into particles, a quaternary alkyl ammonium salt is allowed to disperse into an organic solvent. Thus, even if impurities are present on the surface of crystals of the salt, such impurities will dissolve or disperse into the solvent during the dispersion of the salt into the solvent. The inventive method is, therefore, particularly effective in eliminating impurities from the salt.

(Synthesis of a Quaternary Alkyl Ammonium Salt to be Purified)

An exemplary synthesis of a quaternary alkyl ammonium salt to be purified by the inventive method involves the use of quaternary alkyl ammonium halide or quaternary alkyl ammonium hydroxide as a starting material. The alkyl groups of the starting material are transferred as they are to the quaternary alkyl ammonium salt prepared therefrom. Therefore, the alkyl groups of the starting material should be chosen as appropriate depending on the desired structure and properties of the resulting quaternary alkyl ammonium salt.

To put it more specifically, the alkyl groups constituting the quaternary alkyl ammonium halide or quaternary alkyl ammonium hydoxide which are transferred as they are to the alkyl groups of a resulting quaternary alkyl ammonium salt are not limited to any specific ones. However, from the viewpoint of obtaining a quaternary alkyl ammonium salt with improved electrochemical properties, particularly of obtaining a salt with an enlarged oxidation-reduction potential, alkyl groups with 1 to 5 carbon atoms are preferred. Thus, suitable exemplary alkyl groups include methyl, ethyl, n-propyl, sec-propyl, n-butyl, sec-butyl, tert-butyl, n-pentyl, sec-pentyl, tert-pentyl, etc.

The alkyl groups may be the same with each other. However, from the viewpoint of ensuring an improved effect of the inventive method, or of obtaining a quaternary alkyl ammonium salt with an improved oxidation-reduction potential, at least two of the alkyl groups are preferably different from each other.

One or more of the alkyl groups may be substituted by other substituent(s), unless the substitution interferes with the effect of the invention. Suitable substituents include, for example, benzoic substituent(s) such as benzyl or phenyl, or pyridinium. Among them, pyridinium is particularly preferred.

According to the conventional techniques described above, fluoroboric acid, hydrofluoric acid and boron trifluoride, hydrofluoric acid and phosphorous pentafluoride are allowed to react with quaternary alkyl ammonium halide and/or quaternary alkyl ammonium hydroxide. Then, it is possible to obtain a quaternary alkyl ammonium salt to be purified by the inventive method. Fluoroboric acid, hydrofluoric acid and boron trifluoride, and hydrofluoric acid and phosphorous pentafluoride preferably have a low water content, because then the effect of the invention becomes notable. If the synthesis involves a system based on an aqueous solution, the precipitation of a quaternary alkyl ammonium salt will not proceed satisfactorily because the salt is so soluble to the aqueous solution that the yield will be reduced. However, it is still possible to obtain a highly pure product using such a system. To reduce the water content of the product, it is preferable to use a system based on an alcohol solvent.

It is preferable to obtain a quaternary alkyl ammonium salt to be purified by the inventive method by the method disclosed in a published Japanese Patent Application Publication No. 2001-348388, the method comprising reacting quaternary alkyl ammonium halide with fluoroboric acid in alcohol, and drying the reaction product, thereby eliminating the risk of the reaction product being contaminated with chlorine or bromine derived from the starting material.

If a quaternary alkyl ammonium salt obtained by allowing quaternary alkyl ammonium halide to react with fluoroboric acid is purified by the inventive method, it will be possible to obtain a quaternary alkyl ammonium salt far freer from impurities than is possible with the usage of a quaternary alkyl ammonium salt obtained by a common synthetic method. Similarly, when quaternary alkyl ammonium hydroxide is allowed to react with fluoroboric acid, it is possible to obtain a quaternary alkyl ammonium salt comparatively free from impurities. The effect is notable, and the cardinal reaction is preferably allowed to occur in alcohol.

(Suspension)

The inventive method for the purification of a quaternary alkyl ammonium salt comprises dispersing a quaternary alkyl ammonium salt prepared by one of the various conventional methods into an organic solvent to make it a suspension, this dispersion step enabling the elimination of impurities. The quaternary alkyl ammonium salt is dispersed into an organic solvent to form a suspension or an inhomogeneous system, the insoluble suspended particles are recovered by filtration to be separated from impurities which largely dissolve in the solvent, and the particles are dried. Thus, a quaternary alkyl ammonium salt having impurities largely removed is obtained.

(Organic Solvent)

It is possible to obtain a suspension of a quaternary alkyl ammonium salt by transferring the salt to an organic solvent, and stirring the mixture or leaving the mixture untouched. Suitable organic solvents to receive the suspension are not limited to any specific ones. The weight of the organic solvent with respect to 100 parts by weight of the quaternary alkyl ammonium salt is 10 to 10,000 parts by weight, preferably 10 to 500 parts by weight. If the weight in question of the organic solvent is below 10 parts by weight, the purification effect of the method will be slightly affected. On the other hand, if the weight in question of the organic solvent is over 500 parts by weight, although the purification effect will be invariable, following problems will arise: impurities due to the introduction of the organic solvent will contaminate the coexistent quaternary alkyl ammonium salt, and a partial or entire fraction of the quaternary alkyl ammonium salt will dissolve in the organic solvent.

Suitable organic solvents where a quaternary alkyl ammonium salt is dispersed into a suspension include carbonyl compounds such as acetone, methyl-isobutyl-ketone, etc. Among them acetone is particularly preferred because it allows the efficient dispersion of a quaternary alkyl ammonium salt into a suspension. If a quaternary alkyl ammonium salt is allowed to efficiently disperse into a suspension, it is possible for the impurities adhered to the surface of crystals or entrapped within crystals to be brought into contact with the solvent to be dissolved thereto. This makes it possible to provide quaternary alkyl ammonium salts with a higher purity and thus dielectric capacitors with higher reliability than is possible with conventional methods including no such dispersion.

Combinational use of an alcohol such as methanol, ethanol, 1-propanol, 2-propanol, etc., cyan compound such as acetonitrile, etc., ether such as ethylether, tetrahydrofuran, etc., ester such as ethyl acetate, etc., aliphatic hydrocarbon such as hexane, cyclohexane, etc., may be employed, as long as it does not interfere with the effect of the inventive method.

(Washing After Filtration)

Crystal particles are separated by filtration from the dispersing solvent. Preferably, the particles are washed with an organic solvent so that impurities adhered to the surface of the particles can be removed. Suitable organic solvents to be used for the washing include alcohols such as ethanol, 1-propanol, 2-propanol, etc., ethers such as ethylether, tetrahydrofuran, etc., aliphatic hydrocarbons such as hexane, cylcohexane, etc., carbonyl compounds such as acetone, methyl-isobutyl-ketone, etc., and cyan compounds such as acetonitrile, etc. Among them, one or more chosen from the group comprising ethanol, 1-propanol and 2-propanol are more preferred because solubility of a quaternary alkyl ammonium salt to such a solvent is comparatively low, and impurities can selectively dissolve in such a solvent. The solvent selected as above may be combined with methanol or water. However, to the solvent combined with methanol or water, a quaternary alkyl ammonium salt becomes highly soluble. Therefore, ethanol, 1-propanol or 2-propanol alone is preferably used for the washing. If said solvent is used in combination with another solvent, its content in the solvent system is preferably 20 wt % or higher.

(Drying)

According to the inventive method for the purification of quaternary alkyl ammonium salts, the water content of the quaternary alkyl ammonium salt is reduced by utilizing an azeotropic solvent system. For this purpose, to the solvent system is preferably added one or more chosen from the group comprising acryl amide, ethyl acrylate, acrylonitrile, acetyl acetone, anisole, ethyl benzoate, ethanol, 1-octanol, 2-octanol, octane, formic acid, chlorobenzene, chloroform, ethyl acetate, methyl acetate, carbon tetrachloride, 1,4-dioxane, cyclohexanol, cyclohexanone, cyclohexane, didecane, trimethylamine, toluene, naphthalene, nitroethane, pyridine, phenol, 1-butanol, 2-butanol, furfuryl alcohol, 1-propanol, 2-propanol, 1-hexanol, hexane, hexylamine, 1-heptanol, 3-heptanone, 4-heptanone, benzene, 1-pentanol, 2-pentanol, methyl methacrylate, 2-methylpyridine, 3-methylpyridine, 4-methylpyridine, methyl butyrate, etc. Among them, 1-propanol, 2-propanol, hexane and cyclohexane are particularly preferred because of their enabling the efficient reduction of the water content in the quaternary alkyl ammonium salt to be purified.

(Drying Temperature)

When a quaternary alkyl ammonium salt is obtained as a suspension through the dispersion step, a drying step must be introduced. The temperature required for the drying step is not limited to any specific range, but the drying is performed between 30 and 200° C., preferably between 60 and 150° C., because then moisture is more effectively eliminated from the quaternary alkyl ammonium salt. The drying may be performed under a reduced pressure, or under the normal atmospheric pressure.

According to the inventive method as described above in which a quaternary alkyl ammonium salt is dispersed in an organic solvent to form a suspension there, it is possible to obtain a quaternary alkyl ammonium salt in which the content of water is kept low. Needless to say, if the same process is repeated, it is possible to obtain a quaternary alkyl ammonium salt in which the elimination of moisture is further enhanced, and thus to obtain a more highly purified quaternary alkyl ammonium salt.

(Particulate Salt)

According to the inventive method, it is possible to obtain a quaternary alkyl ammonium salt in the form of particles. The particles preferably have a diameter of 700 μm or less. If the particles have a diameter of 700 μm or less, their water content will exhibit a stepwise reduction in water content. The particles with a diameter of 700 μm or less will also exhibit a stepwise reduction in the content of impurities such as metals. The particles preferably have a diameter of 500 μm or less. The lower limit of the particle diameter is preferably 50 μm because then the particles become easy to handle.

(Concentration of Impurities After Purification)

A quaternary alkyl ammonium salt obtained by a conventional method contains moisture at about 70 ppm. It is possible according to the inventive method to reduce the water content of a quaternary alkyl ammonium salt to 20 ppm or lower. A study was undertaken as to the effect of water content on the performance of the quaternary alkyl ammonium salt, and it was found that, when the water content is reduced to 50 ppm or lower, the oxidation-reduction potential of the electrolytic solution to which the salt is involved is enlarged.

The contamination by a halogen atom is preferably reduced to 5 ppm or lower. The contaminations by Na, Ca, Mg, Al, Fe and Cr are preferably reduced to 1 ppm or lower, respectively.

EXAMPLES

The present invention will be further illustrated by means of representative examples. These examples, however, are cited simply as illustrative examples, and the present invention is not limited in any way by those examples. The following examples are evaluated based on the features revealed by the methods mentioned in the following paragraphs (1) to (5).

(1) Purity: the purity of a test quaternary alkyl ammonium salt was evaluated based on the content of fluorine determined by titration.

(2) Moisture content: the moisture content of a test quaternary alkyl ammonium salt was evaluated by the Karl-Fischer method.

(3) Concentration of chloride ion or bromide ion: the concentration of chloride ion or bromide ion of a test quaternary alkyl ammonium salt was evaluated by nephelometry.

(4) Content of metal impurities: the content of metal impurities of a test quaternary alkyl ammonium salt was evaluated by atomic luminescence analysis.

(5) oxygen-reduction potential: the oxygen-reduction potential of a test quaternary alkyl ammonium salt was evaluated by cyclic voltammetry. The test electrolytic solution was obtained by dissolving triethylmethylammonium tetrafluorobotate/propylenecarbonate (PC) to give a concentration of 1.8 mol/kg.

The evaluations of the moisture content of a test quaternary alkyl ammonium salt and of its oxidation-reduction potential were performed at 25° C. in a nitrogen atmosphere. The other tests were performed in the normal atmosphere.

Example 1

A 2287.5 g (15 mol) of triethylmethylammonium chloride was mixed with 4611 g (corresponding to 15.75 mol of fuloroboric acid) of a solution of 30% fluoroboric acid in methanol, and the mixture was stirred at 60° C. for one hour. The resulting solution was cooled to about 0° C. to allow a sufficient amount of the target compound to be precipitated. The precipitate was recovered by filtration, and dried by being exposed to a nitrogen atmosphere at 105° C. for 12 hours.

A 2295 g (75.3% yield) of triethylmethylammoium tetrafluoroborate was obtained. The purity of the product was 99.8% in terms of the fluorine content. The moisture content of the product was 300 ppm after drying, and the product exists as a solid mass. The concentration of chloride ion of the product was 5 ppm or lower, and the concentration of each metal impurity such as Na, Ca, Mg, Al, Fe, Cr, etc., was 1 ppm or lower.

Example 2

A 501 g of triethylmethylammonium tetrafluoroborate in the form of a solid mass obtained in Example 1 was allowed to disperse at 20° C. for five hours into 1010 g of acetone to make a suspension. The suspended crystals were recovered by filtration, washed with 2-propanol, and dried by being exposed to a nitrogen atmosphere at 105° C. for 12 hours.

The triethylmethylammonium tetrafluoroborate thus obtained existed as crystals (particles) having a diameter of about 300 μm. A 360 g (72.0% yield) of triethylmethylammoium tetrafluoroborate was obtained. The purity of the product was 99.9% in terms of the fluorine content. The moisture content of the product was 20 ppm or lower. The concentration of chloride ion of the product was 1 ppm or lower or the detection limit by nephelometry, and the concentration of each metal impurity such as Na, Ca, Mg, Al, Fe, Cr, etc., was 1 ppm or lower.

The oxidation-reduction potential of the product is shown in Table 1.

Example 3

A 500 g of triethylmethylammonium tetrafluoroborate in the form of a solid mass obtained in the same manner as in Example 1 was allowed to disperse at 20° C. for five hours into a mixture comprising acetone/2-propanol (705 g/400 g) to make a suspension. The suspended crystals were recovered by filtration, washed with 2-propanol, and dried by being exposed to a nitrogen atmosphere at 105° C. for 12 hours.

The triethylmethylammonium tetrafluoroborate thus obtained existed as crystals (particles) having a diameter of about 300 μm. A 395 g (79.0% yield) of triethylmethylammoium tetrafluoroborate was obtained. The purity of the product was 99.9% in terms of the fluorine content. The moisture content of the product was 20 ppm or lower. The concentration of chloride ion of the product was 1 ppm or lower or the detection limit by nephelometry, and the concentration of each metal impurity such as Na, Ca, Mg, Al, Fe, Cr, etc., was 1 ppm or lower.

The oxidation-reduction potential of the product is shown in Table 1.

Example 4

A 763.1 g (5 mol) of triethylmethylammonium tetrafluoroborate was mixed with 1152 g (5.25 mol of fluoroboric acid) of a 40% aqueous solution of fluoroboric acid, and the mixture was stirred at 20° C. for 30 minutes. Then, the system was concentrated by being exposed to nitrogen current at 105° C. for three hours, and cooled to 0° C. to allow a sufficient amount of crystals to precipitate. The suspended crystals were recovered by filtration, and dried by being exposed to nitrogen current at 105° C. for 12 hours.

A 580 g (57.1% yield) of triethylmethylammoium tetrafluoroborate was obtained. The purity of the product was 99.8%. The moisture content of the product after drying was 500 ppm. The product existed as crystals (particles) having a diameter of about 500 μm.

A 500 g of triethylmethylammonium tetrafluoroborate thus obtained existing as particles having a diameter of about 500 μm was allowed to disperse into 270 g of acetone at 20° C. for three hours to make a suspension. The crystals were separated by filtration from the solvent, washed with 2-propanol, and dried by being exposed to nitrogen current at 105° C. for 12 hours.

The triethylmethylammonium tetrafluoroborate thus obtained existed as crystals (particles) having a diameter of about 300 μm. A 470 g (94.0% yield) of triethylmethylammoium tetrafluoroborate was obtained. The purity of the product was 99% in terms of the fluorine content.

The moisture content of the product was 30 ppm or lower. The concentration of chloride ion of the product was 1 ppm or lower or the detection limit by nephelometry, and the concentration of each metal impurity such as Na, Ca, Mg, Al, Fe, Cr, etc., was 1 ppm or lower.

The oxidation-reduction potential of the product is shown in Table 1.

Example 5

A 702.2 g (2.5 mol) of tributylmethylammonium bromide was mixed with 1912 g (2.6 mol of phosphorous hexafluoride) of 20% methanol solution of phosphorous hexafluoride, and the mixture was stirred at 20° C. for 30 minutes. Then, the system was concentrated by being exposed to nitrogen current at 105° C. for three hours, and was cooled to 0° C. to allow a sufficient amount of crystals to precipitate. The suspended crystals were recovered by filtration, and dried by being exposed to nitrogen current at 105° C. for 12 hours.

A 324 g (63.3% yield) of the target product was obtained. The purity of the product was 99.8%. The moisture content of the product after drying was 200 ppm. The product existed as crystals (particles) having a diameter of about 500 μm.

A 250 g of triethylmethylammonium tetrafluoroborate thus obtained existing as crystals (particles) having a diameter of about 500 μm was allowed to disperse into 200 g of acetone at 20° C. for three hours to make a suspension. The crystals were separated by filtration from the solvent, washed with 2-propanol, and dried by being exposed to nitrogen current at 105° C. for 12 hours.

The triethylmethylammonium tetrafluoroborate thus obtained existed as crystals (particles) having a diameter of about 300 μm. A 227 g (90.8% yield) of triethylmethylammoium tetrafluoroborate was obtained. The purity of the product was 99.9% in terms of the fluorine content.

The moisture content of the product was 10 ppm or lower. The concentration of bromide ion of the product was 1 ppm or lower or the detection limit by nephelometry, and the concentration of each metal impurity such as Na, Ca, Mg, Al, Fe, Cr, etc., was 1 ppm or lower.

The oxidation-reduction potential of the product is shown in Table 1.

Comparative Example 1

A 498 g of triethylmethylammonium tetrafluoroborate in the form of a solid mass obtained as in Example 1 was completely dissolved in 3502 g of acetone. The solution was cooled to about 0° C. to allow a sufficient amount of a target product to be precipitated. The crystals were recovered by filtration, and dried by being exposed to nitrogen current at 105° C. for 12 hours. A 323.7 g (65.0% yield) of triethylmethylammoium tetrafluoroborate was obtained. The purity of the product was 99.8% in terms of the fluorine content. The moisture content of the product was 70 ppm. The product was obtained as a solid mass. The concentration of chloride ion was 3 ppm or less. The concentration of each metal impurity such as Na, Ca, Mg, Al, Fe, Cr, etc., was 1 ppm or lower.

The oxidation-reduction potential of the product is shown in Table 1.

TABLE 1

Oxidation-reduction potentials of the products

| | Triethylmethylammonium tetrafluoroborate | | | | Tributylmethylammonium hexafluorophosphate |
|---|---|---|---|---|---|
| | Ex. 2 | Ex. 3 | Ex. 4 | Comp. Ex. 1 | Ex. 5 |
| Shape | Particle | Particle | Particle | Solid mass | Particle |
| Water content (ppm) | 20 | 20 | 30 | 70 | 10 |
| Ox-Red potential (V) | 7.0 | 7.0 | 6.7 | 6.0 | 6.7 |

The following conclusion was obtained from the results. With regard to Comparative Example 1 in which triethylmethylammonium tetrafluoroborate was completely dissolved in acetone to be recrystallized, the product was obtained as a solid mass, and thus it was difficult to keep the water content of the product at a low level. As a consequence, the oxidation-reduction potential of the product remained considerably low which affected the performance of the product.

In contrast, with regard to Examples in which the starting material was dispersed into the organic solvent to make a suspension, the product was obtained as particulate crystals, and thus it was possible to keep the water content of the product at a low level. As a consequence, the oxidation-reduction potential of the product was enlarged.

As is obvious from the results of Examples 1 to 4, when triethylmethylammonium tetrafluoroborate was dispersed in an organic solvent to make a suspension there, it became possible to obtain triethylmethylammonium tetrafluoroborate as particles. In this process, following features were confirmed. 1. In the synthesis of triethylmethylammonium tetrafluoroborate, the starting materials are preferably allowed to react in an alcohol. 2. In the purification of a quaternary alkyl ammonium salt based on its dispersion into an organic solvent, acetone is particularly suitable to be used as such an organic solvent. 3. The product obtained as crystals is preferably washed with an alcohol solvent such as 2-propanol or the like.

Comparison of the results of Example 2 and Example 5 shows that the particulate tetrafluoroborate product having a low water content exhibits a larger oxidation-reduction potential than does the hexafluorophosphate product.

INDUSTRIAL APPLICABILITY

According to the method of the present invention, it is possible to obtain a particulate quaternary alkyl ammonium salt having a low water content at a high yield which is suitably used as an electrolyte in an electrolytic solution, the method comprising dispersing the salt in an organic solvent to cause it to form a suspension there.

The invention claimed is:

1. A method for purifying a quaternary alkyl ammonium salt, the method comprising:
    dispersing a quaternary alkyl ammonium salt to be purified into an acetone solvent to form a suspension of salt particles therein, the quaternary alkyl ammonium salt being one of quaternary alkyl ammonium-tetrafluoroborate and quaternary alkyl ammonium-hexafluorophosphate;
    recovering the quaternary alkyl ammonium salt particles from the acetone solvent; and
    washing the quaternary alkyl ammonium salt particles with an alcohol solvent selected from the group consisting of 1-propanol, 2-propanol and ethanol.

2. The method for purification according to claim 1, wherein the quaternary alkyl ammonium is one of triethylmethylammonium and tributylmethylammonium.

3. The method for purification according to claim 1, wherein the quaternary alkyl ammonium-tetrafluoroborate is triethylmethylammonium tetrafluoroborate and the quaternary alkyl ammonium-hexafluorophosphate is tributylmethylammonium hexafluorophosphate.

4. The method for purification according to claim 1, wherein the quaternary alkyl ammonium salt particles are recovered from the suspension by filtration.

5. The method for purification according to claim 1, further comprising drying the quaternary alkyl ammonium salt particles.

6. A method for purifying a quaternary alkyl ammonium salt, comprising:
dispersing a quaternary alkyl ammonium salt having impurities into an acetone solvent to form a suspension of quaternary alkyl ammonium salt particles in the acetone solvent, the quaternary alkyl ammonium salt being one of quaternary alkyl ammonium-tetrafluoroborate and quaternary alkyl ammonium-hexafluorophosphate, and the quaternary alkyl ammonium salt;
filtering the suspension to separate the quaternary alkyl ammonium salt particles from the acetone solvent; and
washing the quaternary alkyl ammonium salt particles with an alcohol solvent selected from the group consisting of 1-propanol, 2-propanol and ethanol.

7. The method for purification according to claim 6, further comprising drying the quaternary alkyl ammonium salt particles.

8. The method for purification according to claim 6, wherein the quaternary alkyl ammonium is one of triethylmethylammonium and tributylmethylammonium.

9. The method for purification according to claim 6, wherein the quaternary alkyl ammonium-tetrafluoroborate is triethylmethylammonium tetrafluoroborate and the quaternary alkyl ammonium-hexafluorophosphate is tributylmethylammonium hexafluorophosphate.

* * * * *